United States Patent
Snook

(10) Patent No.: US 9,521,959 B2
(45) Date of Patent: Dec. 20, 2016

(54) METHOD AND SYSTEM FOR RETRAINING BRAINWAVE PATTERNS USING ULTRA LOW POWER DIRECT ELECTRICAL STIMULATION FEEDBACK

(71) Applicant: Corey Charles Snook, Mount Dora, FL (US)

(72) Inventor: Corey Charles Snook, Mount Dora, FL (US)

( * ) Notice: Subject to any disclaimer, the term of this patent is extended or adjusted under 35 U.S.C. 154(b) by 775 days.

(21) Appl. No.: 13/887,101

(22) Filed: May 3, 2013

(65) Prior Publication Data

US 2014/0330157 A1    Nov. 6, 2014

(51) Int. Cl.
  *A61B 5/04* (2006.01)
  *A61B 5/0482* (2006.01)

(52) U.S. Cl.
  CPC ......... *A61B 5/0482* (2013.01); *A61B 5/04017* (2013.01)

(58) Field of Classification Search
  None
  See application file for complete search history.

(56) References Cited

U.S. PATENT DOCUMENTS

| | | | |
|---|---|---|---|
| 3,393,279 A | 7/1968 | Flanagan | |
| 4,928,704 A | 5/1990 | Hardt | |
| 5,406,957 A | 4/1995 | Tansey | |
| 6,081,743 A | 6/2000 | Carter et al. | |
| 7,269,456 B2 | 9/2007 | Collura | |
| 8,265,761 B2 | 9/2012 | Siever | |
| 8,280,502 B2 | 10/2012 | Hargrove et al. | |
| 2005/0024051 A1* | 2/2005 | Doddrell | G01R 33/56518 324/307 |
| 2008/0208008 A1* | 8/2008 | Turner | A61B 5/0006 600/300 |

\* cited by examiner

*Primary Examiner* — Etsub Berhanu
(74) *Attorney, Agent, or Firm* — IPLA P.A.; James E. Bame

(57) ABSTRACT

A method of retraining brainwave patterns using direct electrical stimulation feedback comprises: securing two or more electrodes to a subject's scalp and/or ears; acquiring EEG signal(s) on at least one channel; amplifying the EEG signal or signals via differential amplifier means; digitizing said EEG signal or signals via Analog-to-Digital converter means; selecting at least one of said channels from which to derive feedback; creating at least one digital-domain representation of said selected EEG signal or signals; creating a signal or signals representing at least one time-domain "distortion" of said digital domain representation or representations by time distortion means; differentiating said time distorted signal or signals; and introducing said differentiated signal or signals back onto the pairs of input leads via coupling means, wherein said differentiated signal or signals are thus input directly to the brain and nervous system, bypassing the normal systems of perception.

12 Claims, 3 Drawing Sheets

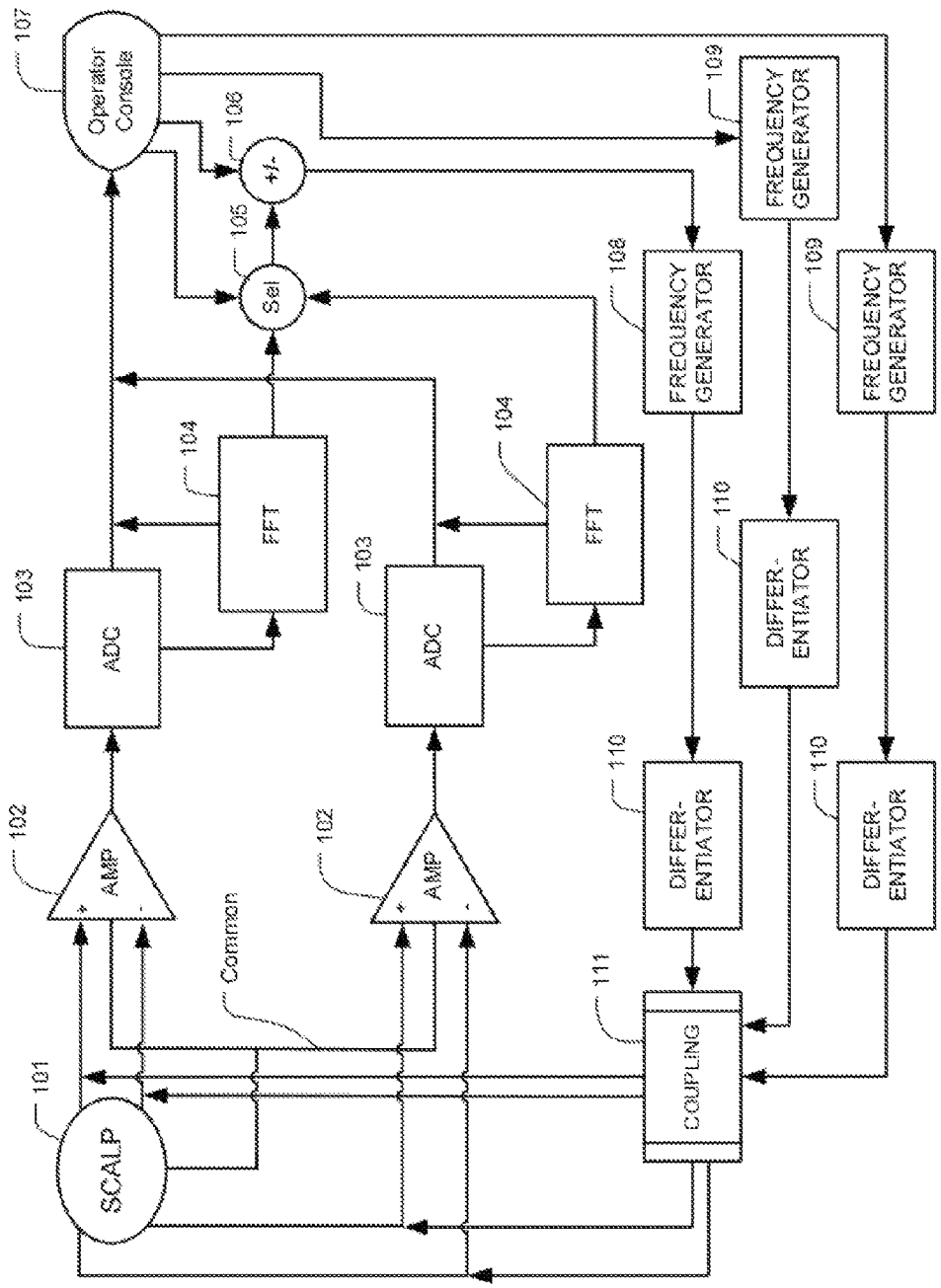

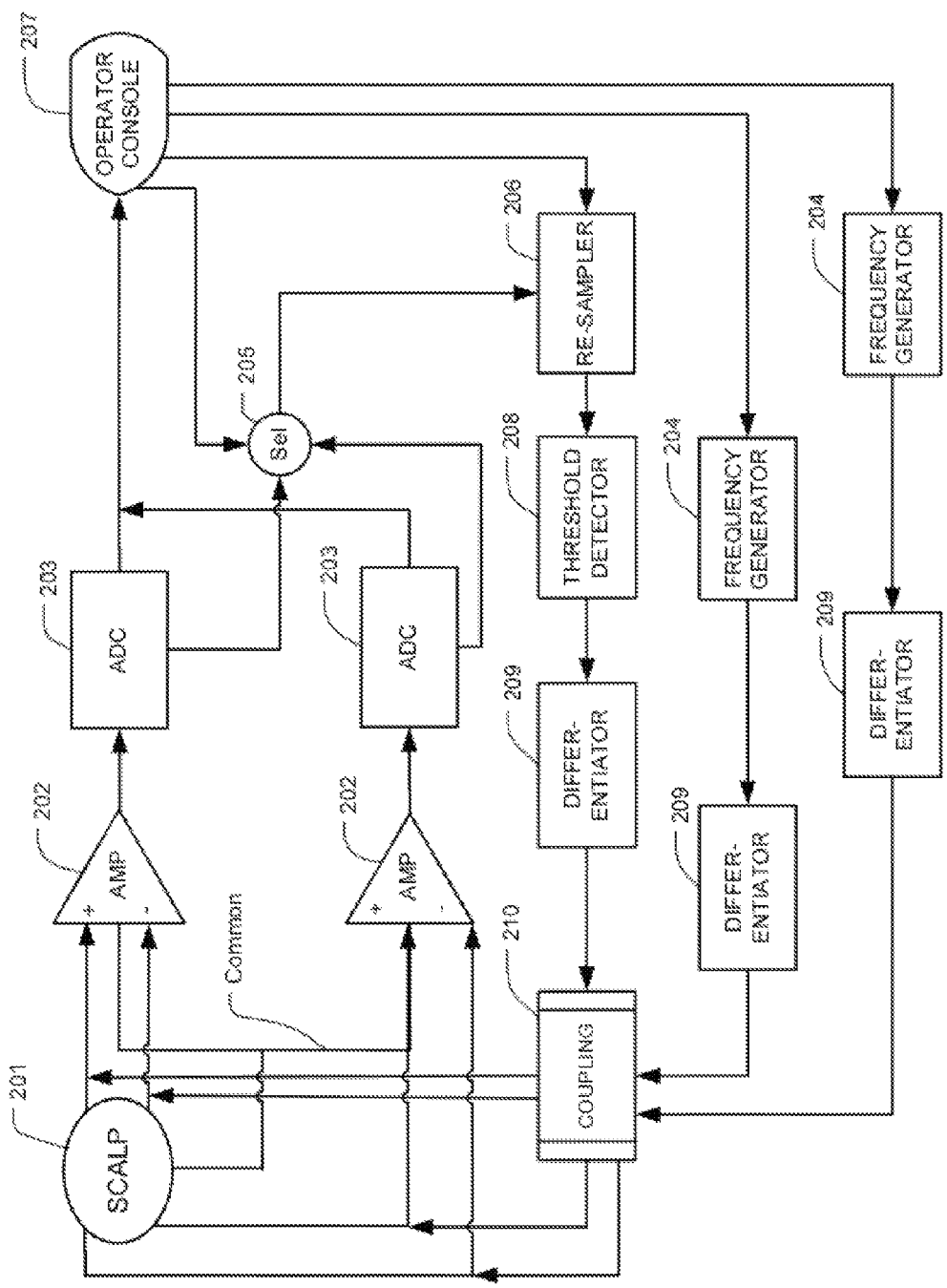

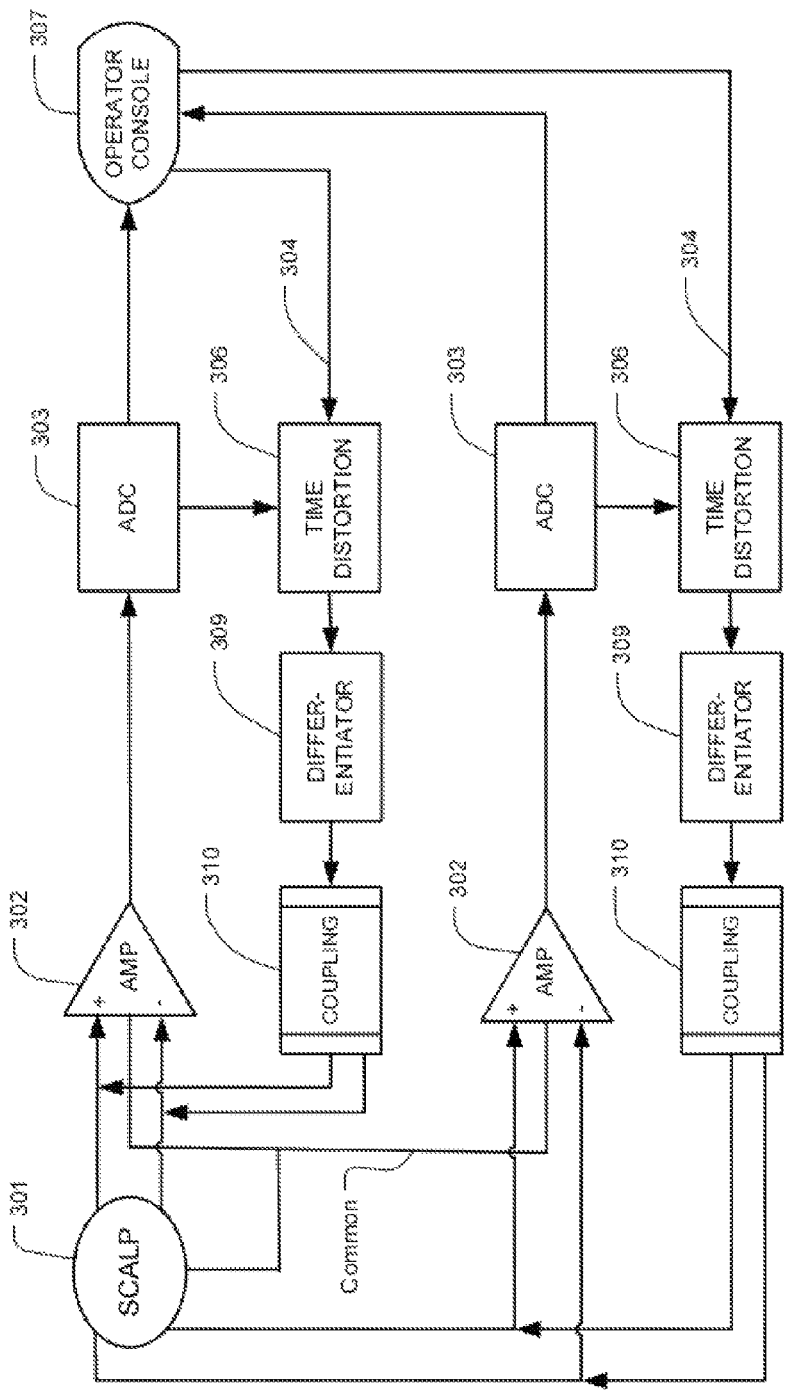

METHOD AND SYSTEM FOR RETRAINING BRAINWAVE PATTERNS USING ULTRA LOW POWER DIRECT ELECTRICAL STIMULATION FEEDBACK

BACKGROUND OF THE INVENTION

1. Field of the Invention

The field of the invention is direct neurofeedback.

2. Description of Related Art

In the field of neurofeedback, cranio-electrostimulation (CES), and "light and sound" machines, there are teachings of applying signals to the brain, either directly in the form of currents, as in the case of CES, or indirectly through audio or visual channels, in an effort to alter the dominant brainwave patterns and thereby effect improvement in individual functioning. In general, CES (e.g., Siever 761) does not seek to relate the generated signal to a specific pre-existing EEG frequency, while neurofeedback has used perceptible feedback signals (e.g. light or sound) with the goal of entraining the brain to an alternate pattern (e.g., Carter 858, Collura 456), or simply providing an indication that the brainwaves are shifting in a presumably desired direction (Tansey 957, Hardt 704). Flanagan 279 teaches that only the differentiated edges of the signal are necessary for neuronal recognition, while Hargrove 502 attempts to get EEG band signals into the brain with a form of pulse-width modulation, but misses the point of what the brain discerns as frequency, as described by Flanagan. The present invention seeks to build on some of these underlying principles and clinical successes, and to provide a unique and very high performance direct feedback system based on an even more current understanding of overall nervous system response, including Central, Glial, Sympathetic and Parasympathetic Nervous Systems.

BRIEF SUMMARY OF THE INVENTION

A method and system for retraining brainwave patterns to promote higher and more adaptive functioning using ultra low power direct electrical stimulation feedback is herein described. Relatively small Electroencephalographic (EEG) signals are acquired by electrically connecting 2 or more leads to the scalp of a client. Each channel to be acquired requires an Active (+) lead, a Reference (−) lead and a Common lead. The common lead may be connected almost anywhere on the body that is convenient, but preferable sites include the back of the neck, the ear, the face and the scalp. For multi-channel systems, the common lead is shared, and more than one channel may share a "linked" reference (−) lead, depending on the configuration desired. These leads conduct EEG signals to a "front-end", comprising one or more instrumentation amplifiers, one for each channel, or signal, to be acquired. These amplifiers typically have high common-mode rejection (CMMR) ratios, so that very little more than difference signals are amplified. The front end optionally may be followed by one or more stages of amplification. The amplified signal is then fed to an analogue-to-digital converter (ADC), typically comprising a sample-and-hold circuit, followed by the digitizing circuit. The output of the ADC is typically fed to a digital processor as a sequence of values, each representing a sample of the input signal at a specific point in time. Within the digital processor are algorithms for further processing and analyzing the digitized EEG signal, typically to extract one or more characteristics of the EEG signal for further processing or analysis, for example by use of digital filters and/or Fast Fourier Transforms (FFTs). These techniques are all well known in the current art, and are generally summarized as "signal acquisition and analysis".

In one embodiment of the present invention, at least one EEG input channel is selected from which to derive feedback, either through manual selection, for example, via computer screen, keyboard and/or pointer device, or, as one possible alternative, through a prepared program or script specifying various parameters, including which channel or channels are selected for each time period.

A digital-domain representation is thus created of one or more selected EEG signals. A time-domain "distortion", that is, either faster or slower, of the resultant digital-domain representation is then accomplished by one of any of a number of means well known in the art, for example using a Fast Fourier Transform (FFT) to extract a peak, dominant, or modal frequency, and then regenerating a faster or slower version of the extracted frequency by means of a waveform generator. Another time-domain distortion means could be re-sampling the digitized waveform to yield a waveform of similar shape, but whose frequency would be sped up or slowed down by the ratio of input to output sample frequencies. The time-domain distortion signal thus created is converted directly or indirectly to a series of very short pulses whose spacing would represent the zero-crossings of one or more of the newly derived time-distorted frequencies. These pulses are further differentiated and coupled back onto one or more pairs of input leads, (both Active (+) and Reference (−) with respect to Common), which couplers may optionally may be provided with resonant circuits utilizing inductance and capacitance to induce an oscillation on the leading and possibly trailing edges of the pulses to further improve skin conduction. The resulting signal contains extremely low power, that is, "ultra low power", but according to recent experience and current understanding, would activate one or more of the mentioned nervous systems of either humans or other vertebrates, with the intent to encourage nervous system normalization while minimizing the likelihood of undesirable reactions. The signal is so low in power that it is imperceptible directly, but on rare occasion the client may be aware of a sensation caused by the changes being produced, for example, normalized blood flow, nerve function, or autonomic balance. It requires no effort on the part of the client, and may therefore be useful in situations in which the client is unconscious or otherwise incapable of conscious cooperation.

It may also be desirable and beneficial to incorporate one or more additional, essentially fixed frequency signal components which are similarly differentiated and shaped as previously described.

The described system has been utilized effectively in human trials, and some other vertebrate trials, including horses and dogs. The robust results have profound implications in the restoration of nervous system balance and function in both humans and animals, particularly following brain injury.

BRIEF DESCRIPTION OF THE DRAWINGS

The drawings illustrate the best modes presently contemplated of carrying out the invention, wherein:

FIG. 1 is a block diagram of the hardware components of Embodiment #1 of the present invention;

FIG. 2 is a block diagram of the hardware components of Embodiment #2 of the present invention; and FIG. 3 is a block diagram of the hardware components of Embodiment #3 of the present invention.

DETAILED DESCRIPTION OF THE INVENTION

With reference to FIG. 1, Embodiment #1, there is illustrated one preferred embodiment, which includes the basic components necessary for EEG data acquisition and analysis, illustrated for two channels. The EEG signal is picked up at the client's scalp, 101, and conducted over preferably shielded EEG cables to one or more Amplifiers, 102. The amplified signal is further processed by one or more Analog-to-Digital Converters (ADCs), 103. The output from each ADC feeds both a set of filters, 104, including a Fast Fourier Transform (FFT), and also an operator display screen, 107. The output of the filters is fed to a selection means, 105, which may be controlled by the operator, as illustrated, or by a program/script. The selected filter output, preferably an FFT, feeds preferably an adder, 106, in order to create the time distortion. The second adder input, which provides control over the amount of distortion, is controlled by either the operator, or by a program/script. Both adder inputs are numerical values in this embodiment. The output of the adder, also a numerical value representing a frequency which has been distorted from the EEG frequency, controls a Frequency Generator, 108, which preferably generates a square wave. That waveform is differentiated by function 110 and coupled by function 111 back onto the input leads, and thus back to the scalp. A multiplicity of essentially fixed frequency Frequency Generators, 109, controlled by either operator or programmatically, for example, by a script, generate a square waveform. Those square waveforms are differentiated by differentiator functions 110 and coupled by coupling function 111 back onto the input leads, and thus back to the scalp. Note that in some embodiments, including a preferred embodiment, the coupling and differentiation may be performed by the same components. Note also that whereas the EEG signal is developed differentially across the +/− inputs to the Amplifier or Amplifiers, 102, the coupling is designed to deliver essentially a copy of the same signal to both the plus and minus leads of each pair of input channels, which in-phase signal the differential amplifiers are designed to reject.

With reference to FIG. 2, Embodiment #2, there is illustrated a second embodiment, which includes the basic components necessary for EEG data acquisition and analysis, illustrated for two channels. The EEG signal is picked up at the client's scalp, 201, and conducted over preferably shielded EEG cables to the Amplifier or Amplifiers, 202. The amplified signal is further processed by the Analog-to-Digital Converter or Converters, ADC, 203. The output of the ADC is also fed to an operator display screen, 207, and also to a selection means, 205, which may be controlled by the operator, as illustrated, or by a program/script. The selected ADC output feeds a re-sampler, 206, in order to create the time distortion. The second re-sampler input, which provides control over the amount of distortion, is a numerical value controlled by either the operator, or by a program/script. The output of the re-sampler feeds a threshold detector, 208, that generates a square pattern containing the same time-distorted frequencies as the re-sampled waveform. That square waveform is differentiated by differentiator function 209 and coupled by coupling function 210 back onto the input leads, and thus back to the scalp. A multiplicity of essentially fixed frequency Frequency Generators, 204, controlled either by an operator or programmatically, for example, by a script, generate a square waveform. Those square waveforms are differentiated by Differentiator functions 209 and coupled by Coupling function 210 back onto the input leads, and thus back to the scalp. Note that in some embodiments, the coupling and differentiation may be performed by the same components. Note also that whereas the EEG signal is developed differentially across the +/− inputs to the Amplifier or Amplifiers, 202, the coupling is designed to deliver essentially a copy of the same signal to both the plus and minus leads of each pair of input channels, which in-phase signal the differential amplifiers are designed to reject.

With reference to FIG. 3, Embodiment #3, there is illustrated a third embodiment, which includes the basic components necessary for EEG data acquisition and analysis, illustrated for two channels. The EEG signal is picked up at the client's scalp, 301, and conducted over preferably shielded EEG cables to the Amplifier or Amplifiers, 302. The amplified signal is further processed by the Analog-to-Digital Converter or Converters, ADC, 303. The output of the ADC is also fed to an Operator Console, 307. The operator, and/or a program/script, controls a regeneration function within the firmware/software that creates the time distortion and outputs a square wave of the corresponding distorted frequency. Each ADC output feeds a Time Distortion function, 306, in firmware/software. The second Time Distortion input, 304, which provides control over the amount of distortion, is a numerical value controlled either by the operator, or by a program/script. The square wave output of the time distortion feeds a Differentiator function 309, whose output is then coupled by Coupling function 310 back onto the pairs of input leads, and thus back to the scalp. Note that in some embodiments, the coupling and differentiation may be performed by the same components. Note also that whereas the EEG signal is developed differentially across the +/− inputs to each of the Amplifiers, 302, the coupling is designed to deliver essentially a copy of the same signal to both the plus and minus leads of each pair of input channels, unique to each channel, which in-phase signal pairs the differential amplifiers are designed to reject.

The invention claimed is:

1. A method of retraining brainwave patterns using direct electrical stimulation feedback, comprising the steps of:
    securing two or more electrodes to a subject's scalp and/or ears;
    acquiring EEG (electroencephalography) signal(s) on at least one channel (each channel consisting of an active (+) lead, a reference (−) lead and utilizing a common lead connected somewhere on said subject's body);
    amplifying the EEG signal or signals via differential amplifier means;
    selecting at least one of said channels from which to derive feedback;
    creating at least one digital-domain representation of said selected EEG signal or signals, wherein said digital-domain representation is created by using an analog-to-digital converter;
    creating a signal or signals representing at least one time-domain "distortion" (i.e., either faster or slower) by either performing a Fast Fourier Transform (FFT) or by re-sampling said digital domain representation or representations;
    differentiating said time distorted signal or signals; and
    introducing said differentiated signal or signals back onto pairs of input leads via coupling means, wherein said differentiated signal or signals are thus input directly to the brain and nervous system.

2. A method according to claim 1, in which the differentiated signal comprises a sequence of spikes or pulses of no more than 100 microseconds duration.

3. A method according to claim 1, in which the differentiated signal comprises a sequence of spikes or pulses of both positive and negative polarity.

4. A method according to claim 1, in which at least two channels of EEG input are utilized for both EEG signal acquisition and feedback.

5. A method according to claim 1, in which differentiating and coupling means comprise symmetric capacitive coupling to the EEG input leads.

6. A method according to claim 1, in which the coupling means comprise inductive coupling to the EEG inputs.

7. A method according to claim 1, in which at least one additional signal is further generated, differentiated, and coupled to the input leads, wherein said additional signal comprises a fundamental frequency in the range of 800 Hz to 200 KHz.

8. A method according to claim 1, in which the feedback signal is activated from 80 percent to 100 percent of the time a lead is connected to the subject's scalp.

9. A method according to claim 1, in which at least two additional signals are further generated, differentiated, and coupled to input leads.

10. A method according to claim 9, in which at least one of the said two additional signals comprises a fundamental frequency in the range of 10 KHz to 200 KHz.

11. A method according to claim 9, in which at least one of the said two additional signals comprises a fundamental frequency in the range of 800 Hz to 2400 Hz.

12. A system for retraining brainwave patterns using direct electrical stimulation feedback, comprising:
two or more electrodes configured to be secured to a subject's scalp and configured to acquire EEG signal(s) on at least one channel (each channel consisting of an active (+) lead, a reference (−) lead and utilizing a common lead);
second components for selecting at least one of said channels from which to derive feedback;
third components for creating digital-domain representations of at least the selected EEG signal or signals, wherein said digital-domain representation is created by using an analog-to-digital converter;
fourth components for creating a signal or signals representing a time-domain "distortion" (i.e. either faster or slower) by either performing a Fast Fourier Transform (FFT) or by re-sampling said digital domain representation or representations;
one or more differentiating components for creating a differentiated signal or signals and fed by said time distorted signal or signals; and
two or more coupling components for introducing said differentiated signal or signals back onto pairs of input leads, wherein said differentiated signal or signals are thus input directly to the brain and nervous system.

* * * * *